United States Patent
Pergola (10) Patent No.: US 10,645,502 B2
(45) Date of Patent: May 5, 2020

(54) SPANNING CONNECTOR FOR IMPLANTABLE HEARING INSTRUMENT

(75) Inventor: Nicholas Pergola, Arvada, CO (US)

(73) Assignee: Cochlear Limited, Macquarie University, NSW (AU)

( * ) Notice: Subject to any disclaimer, the term of this patent is extended or adjusted under 35 U.S.C. 154(b) by 3559 days.

(21) Appl. No.: 12/268,247

(22) Filed: Nov. 10, 2008

(65) Prior Publication Data

US 2009/0124849 A1 May 14, 2009

Related U.S. Application Data

(60) Provisional application No. 60/986,523, filed on Nov. 8, 2007.

(51) Int. Cl.
*H04R 25/00* (2006.01)
*A61F 2/18* (2006.01)

(52) U.S. Cl.
CPC ...... *H04R 25/606* (2013.01); *A61F 2002/183* (2013.01)

(58) Field of Classification Search
CPC .......................... H04R 25/606; A61F 2002/183
USPC ....................... 600/25; 128/897–899; 623/10
See application file for complete search history.

(56) References Cited

U.S. PATENT DOCUMENTS

| | | | |
|---|---|---|---|
| 4,281,419 A * | 8/1981 | Treace | 623/10 |
| 5,531,787 A * | 7/1996 | Lesinski et al. | 623/10 |
| 5,836,863 A | 11/1998 | Bushek et al. | |
| 6,001,129 A * | 12/1999 | Bushek et al. | 623/10 |
| 6,099,462 A | 8/2000 | A'wengen | |
| 6,139,488 A * | 10/2000 | Ball | 600/25 |
| 6,325,755 B1 * | 12/2001 | Bushek et al. | 600/25 |
| 6,381,336 B1 | 4/2002 | Lesinski | |
| 6,398,717 B1 * | 6/2002 | Leysieffer et al. | 600/25 |
| 6,540,662 B2 * | 4/2003 | Kroll et al. | 600/25 |
| 6,705,985 B2 | 3/2004 | Easter et al. | |
| 6,730,015 B2 | 5/2004 | Schugt et al. | |
| 6,945,999 B2 | 9/2005 | Schneider et al. | |
| 7,278,963 B2 | 10/2007 | Schneider | |
| 7,297,101 B2 | 11/2007 | Neisz et al. | |
| 2004/0147804 A1 * | 7/2004 | Schneider et al. | 600/25 |
| 2007/0021833 A1 * | 1/2007 | aWengen et al. | 623/10 |
| 2008/0019542 A1 * | 1/2008 | Menzel et al. | 381/151 |

* cited by examiner

*Primary Examiner* — Navin Natnithithadha
*Assistant Examiner* — Sunita Reddy
(74) *Attorney, Agent, or Firm* — Pilloff Passino & Cosenza LLP; Martin J. Cosenza (57) ABSTRACT

Provided herein are various connectors that allow for translating the axial movement of an implantable hearing transducer from a first direction to a second direction. In various arrangements, these connectors form a spanning connector that extend across a portion of a tympanic cavity of a patient. One end of the connector can be affixed to the tympanic cavity, and a second end may engage an auditory component. In such an arrangement, a vibratory actuator may engage the connector between the first and second ends. Such an arrangement can provide improved alignment of actuator movement with a direction of movement of an auditory component.

33 Claims, 6 Drawing Sheets

SPANNING CONNECTOR FOR IMPLANTABLE HEARING INSTRUMENT

CROSS REFERENCE TO RELATED APPLICATION

This application claims the benefit of the filing date of U.S. Provisional Application No. 60/986,523 entitled "Spanning Connector for Implantable Hearing Instrument" having a filing date of Nov. 8, 2007, the entire contents of which are incorporated herein by reference.

FIELD OF THE INVENTION

The present invention relates to an apparatus and method (i.e., utility) for interfacing an implantable hearing instrument with a patient's auditory system. More particularly, the utility permits efficient coupling of mechanical transducer to an auditory component when the mechanical transducer and auditory component are misaligned.

BACKGROUND OF THE INVENTION

In the class of hearing aid systems generally referred to as implantable hearing instruments, some or all of various hearing augmentation componentry is positioned subcutaneously on or within a patient's skull, typically at locations proximate the mastoid process. In this regard, implantable hearing instruments may be generally divided into two sub-classes, namely semi-implantable and fully implantable. In a semi-implantable hearing instrument, one or more components such as a microphone, signal processor, and transmitter may be externally located to receive, process, and inductively transmit an audio signal to implanted components such as a transducer. In a fully implantable hearing instrument, typically all of the components, e.g., the microphone, signal processor, and transducer, are located subcutaneously. In either arrangement, an implantable transducer is utilized to stimulate a component of the patient's auditory system (e.g., ossicles, oval window and/or the cochlea).

Implantable hearing instruments are typically classified by the portion of the ear for which they are operative to stimulate. For instance, middle ear hearing instruments are designed to stimulate the auditory components of the middle ear, which includes the tympanic cavity, the tympanic membrane (eardrum) and three small bones called the auditory ossicles. The tympanic cavity is an air filled space that separates the external ear (ear canal) and the inner ear (cochlea). In a healthy ear, the ossicles bones (malleus, incus and stapes) form a bridge or ossicular chain across the tympanic cavity connecting the eardrum to the inner ear/oval window and function to transmit vibrations between these auditory components.

Known implantable hearing aid devices include those which utilize implanted electromechanical transducers positioned within the middle ear (i.e., middle ear transducer) for stimulation of the ossicular chain and/or oval window (see e.g., U.S. Pat. No. 5,702,342). Middle ear transducers typically include a vibratory actuator that interfaces with and stimulates the ossicular chain of the patient via physical engagement. In this regard, one or more bones of the ossicular chain are made to mechanically vibrate, which causes the ossicular chain to stimulate the cochlea through its natural input, the oval window.

As may be appreciated, the utilization of an implantable hearing aid actuator of the above-noted nature entails surgical positioning of the vibratory actuator. Such positioning is typically within the mastoid process of a patient's skull and requires the insertion of the vibratory actuator through a hole formed in the mastoid process and extending into the tympanic cavity, which is also sometimes referred to as the 'attic.' Due to the position of the ear canal, the hole formed through the mastoid process generally intersects the tympanic cavity in a region of the attic where the incus and malleus are found. In this case, the vibratory actuator may be coupled to the ossicles during mounting and positioning of the transducer within the patient. In one example, such coupling may occur via a small aperture formed in the incus bone.

SUMMARY OF THE INVENTION

In many instances patients do not have a healthy middle ear anatomy and/or it is desirable to interface to an auditory component located distally from the attic. In such instances, aligning the vibratory actuator of the middle ear transducer with the auditory transducer remains problematic.

That is, a number of people who exhibit a moderate or greater degree of hearing loss are affected by complications to the conductive components of the middle ear. Sound cannot pass effectively through the middle ear to the cochlea and auditory nerve. Such complications may arise due to disease such as otosclerosis where abnormal growth of bone affects the function of the ossicles, or aural atresia where no external ear canal or tympanic membrane exists. Further, the interconnection between the ossicle bones may be degraded to a point that these bones no longer effectively transmit vibratory signals. In these and other instances, it has been determined that direct interconnection to the stapes, oval window and/or round window may allow for bypassing malformed, missing and/or degraded ossicle bones and thereby provide for improved transmission of vibratory signals.

To interconnect a middle ear transducer to the stapes, the stapes footplate, oval window and/or round window, an implantable hearing instrument will typically access the attic region of the tympanic cavity through the mastoid process. However, access to the attic region of the tympanic cavity may not provide direct access to the stapes/windows region. In this regard, the axis of movement of an actuator of an implantable hearing instrument may not align linearly with the auditory component of interest. Of note, the stapes works similarly to a piston to displace fluid within the cochlea via its interface with the oval window. Movement of the stapes in a direction that is substantially normal to the interface between the stapes and oval window is a near natural movement in a health ear and typically provides the most effective/efficient auditory stimulation. Accordingly, the non-linear alignment of a movement axis of a vibratory actuator device relative to that interface may result in reduced vibratory transfer and, hence, reduced auditory stimulation.

Accordingly, provided herein are systems and methods (utilities) that allow for interconnecting an actuator device with an auditory component such that the auditory component may move in a substantially natural direction even if the axis of movement of the actuator device is not aligned with the direction of natural movement of the auditory component.

According to one aspect, a spanning connector is provided that extends across a portion of the tympanic cavity. A first end of the connector may be fixedly attached to, for example, wall of the tympanic cavity. A second end of the connector may engage an auditory component. A body portion of the connector between its first and second ends may be engaged by a vibratory actuator. Accordingly, the vibratory actuator may displace or deflect the spanning connector such that the second end moves relative to the auditory component it engages. By selectively positioning and/or shaping the connector, axial displacements of an actuator in a first direction may be translated by the second end of the connector to a second direction (e.g., at least partially transverse to the first direction), which may be more closely aligned with a natural direction of movement of the auditory component. To effect movement of the second end in the second direction, the connector may, in one arrangement, be a nonlinear element. That is, at least a portion of the body of the connector may be offset from a reference line extending between the first and second ends of the connector. By way of example only, a portion of the body may be acute, curved or otherwise bent.

The second end of the connector that contacts the auditory component may engage the auditory component in any appropriate manner. In one arrangement, this end of the connector may be disposed against (e.g., biased against) a surface of, for example, an ossicle bone, the oval window or the round window. In other arrangements, this contact end may clip to or straddle a portion of an auditory component (e.g., ossicles). In one specific arrangement, the contact end may engage the stapes head using, for example, a recessed (e.g., cup or bell shaped) coupler. Alternatively, the connector may interconnect to the stapes footplate using, for example, a straight wire that may be inserted into a shallow hole formed within the footplate. In another arrangement, a detachable connector may be utilized. In this arrangement, a first portion of the connector may be permanently affixed to the auditory component. A second portion of the connector may releasably engage the first portion. Accordingly, this may permit selective removal of the hearing instrument without further disturbing the patient's auditory system.

The first end of the connector may be attached to a stationary structure of the middle ear (e.g., tympanic cavity wall) in any appropriate manner. In one arrangement, the first end of the connector includes one or more apertures that may be utilized to fixedly connect the first end to a bone structure. For instance, such apertures may receive one or more bone screws. Likewise, one or more apertures may allow for oseointegration of the first end of the connector with underlying bone structure.

In a further arrangement, a connector may include one or more joints along its length. In this regard, two or more sections of the connector may be permitted to flex relative to one another in response to an applied deflection by an actuating device. Such joints may be integrally formed along the lengths of the connector including, for example, sections having reduced cross-sectional dimensions in relation the remainder of the connector. Alternatively, the joints may be formed as hinged joints or otherwise movable joints.

According to another aspect of the present invention, a hearing instrument that utilizes a spanning connector is provided for transmitting movement of a hearing instrument to an auditory component of a patient. The connector includes an elastic member having a first end for interconnection to a stationary middle ear structure and a second end adapted for interconnection to an auditory component. In a nonbiased state, the elastic member may apply a static load between the stationary middle ear structure and the auditory component. The hearing instrument further includes an actuator that physically engages the elastic member between its first and second ends. The actuator is operative to move at least in a first direction to apply a biasing force to the elastic member. In response to such biasing force, the second end of the elastic member moves in a second direction that is at least partially transverse to the direction of the biasing force.

In one arrangement, the static load between the first and second ends may be negligible or near negligible. In further arrangements, the static load between the first and second ends may be selected to provide a compression load to an auditory component.

In one arrangement, the elastic member is an elongated member. This elongated member may further be plastically deformable in response to an applied stress in order to shape the member for placement within a patient's tympanic cavity. Once deformed to a desired shape, the elastic member may retain elasticity that allows elastic deformation in response to displacement by the actuator.

According to another aspect, a method is provided for use in stimulating an auditory component using an implantable hearing aid transducer. The method includes affixing a first portion of a connector to a stationary middle ear surface and engaging a second portion of the connector with an auditory component. A vibratory actuator may then contact a portion of the connector between the first and second ends. Such vibratory actuator may be displaceable in response to the operation of an implantable hearing aid transducer. Once contacting the connector, the vibrator actuator may be displaced in a first direction in response to auditory stimulation signals received by the transducer. This displacement in the first direction may be translated into the second direction by the second portion of the connector. Such first and second directions may be at least partially transverse.

DETAILED DESCRIPTION OF THE INVENTION

Reference will now be made to the accompanying drawings, which at least assist in illustrating the various pertinent features of the present invention. The following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
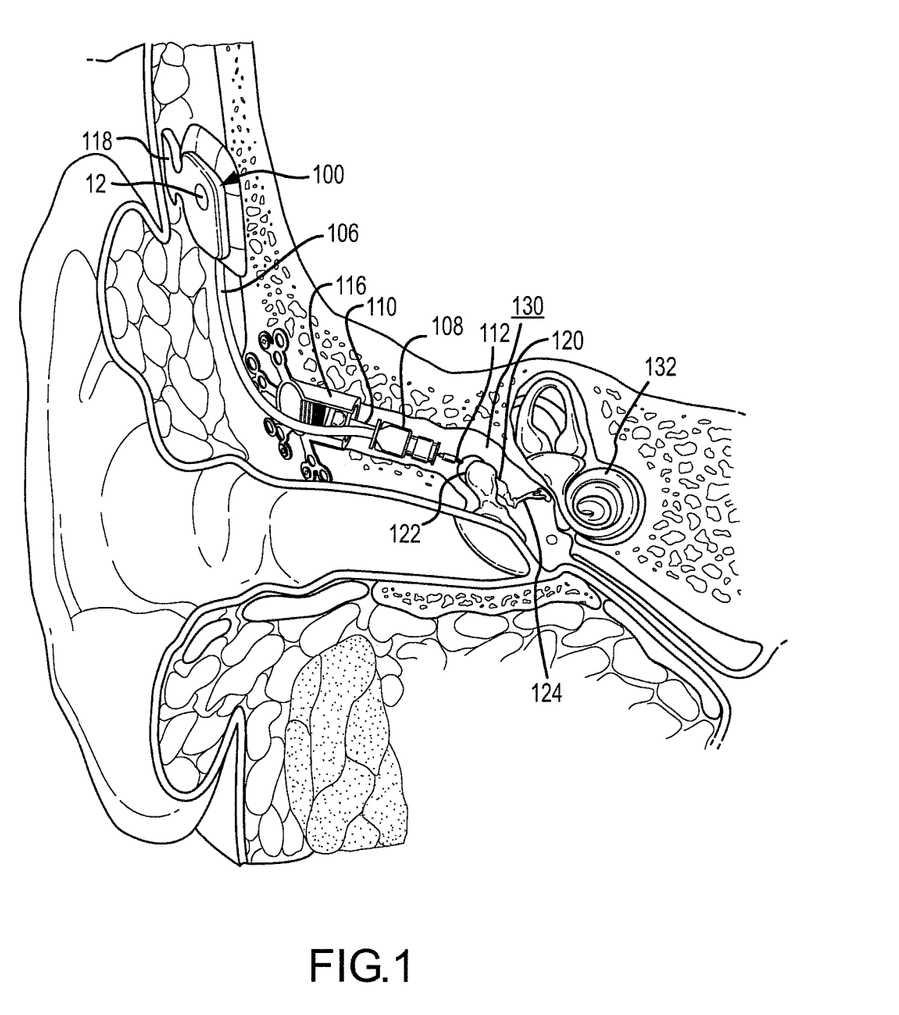
FIG. 1 illustrates a fully implantable hearing instrument.

FIG. 1 illustrates one application of the present invention. As illustrated, the application illustrates a fully implantable hearing instrument. However, it will be appreciated that certain aspects of the present invention may be employed in conjunction with semi-implantable hearing instruments as well. Therefore, the illustrated application is for purposes of illustration and not limitation.

As illustrated, a biocompatible implant housing 100 is located subcutaneously on a patient's skull. The implant housing 100 includes a signal receiver 118 (e.g., including a coil element) and a microphone 12 that is positioned to receive acoustic signals through overlying tissue. The implant housing 100 may be utilized to house a number of components of the fully implantable hearing instrument. For instance, the implant housing 100 may house an energy storage device, a microphone transducer, and a signal processor. Various additional processing logic and/or circuitry components may also be included in the implant housing 100 as a matter of design choice. Typically, the signal processor within the implant housing 100 is electrically interconnected via wire 106 to a transducer 108.

The transducer 108 is supportably connected to a positioning system 110, which in turn, is connected to a bone anchor 116 mounted within the patient's mastoid process (e.g., via a hole drilled through the skull). The transducer 108 includes a vibratory actuator 112 for transmitting vibrations from the transducer 108 to an auditory component of the patient. As shown, the vibratory actuator 112 extends into the tympanic cavity 130 of the patient at a location near where the malleus 122 and incus 120 connect. This region is sometimes referred to as the attic region.

During normal operation, acoustic signals are received subcutaneously at the microphone 12. Upon receipt of the acoustic signals, a signal processor within the implant housing 100 processes the signals to provide a processed audio drive signal via wire 106 to the transducer 108. As will be appreciated, the signal processor may utilize digital processing techniques to provide frequency shaping, amplification, compression, and other signal conditioning, including conditioning based on patient-specific fitting parameters. The audio drive signal causes the transducer 108 to transmit vibrations at acoustic frequencies to the vibratory actuator 112, which is connected to an auditory component to effect the desired sound sensation via mechanical stimulation of the auditory component. This mechanical stimulation is transmitted to the cochlea 132 via the oval window 128. See FIG. 2.

Figure 2:
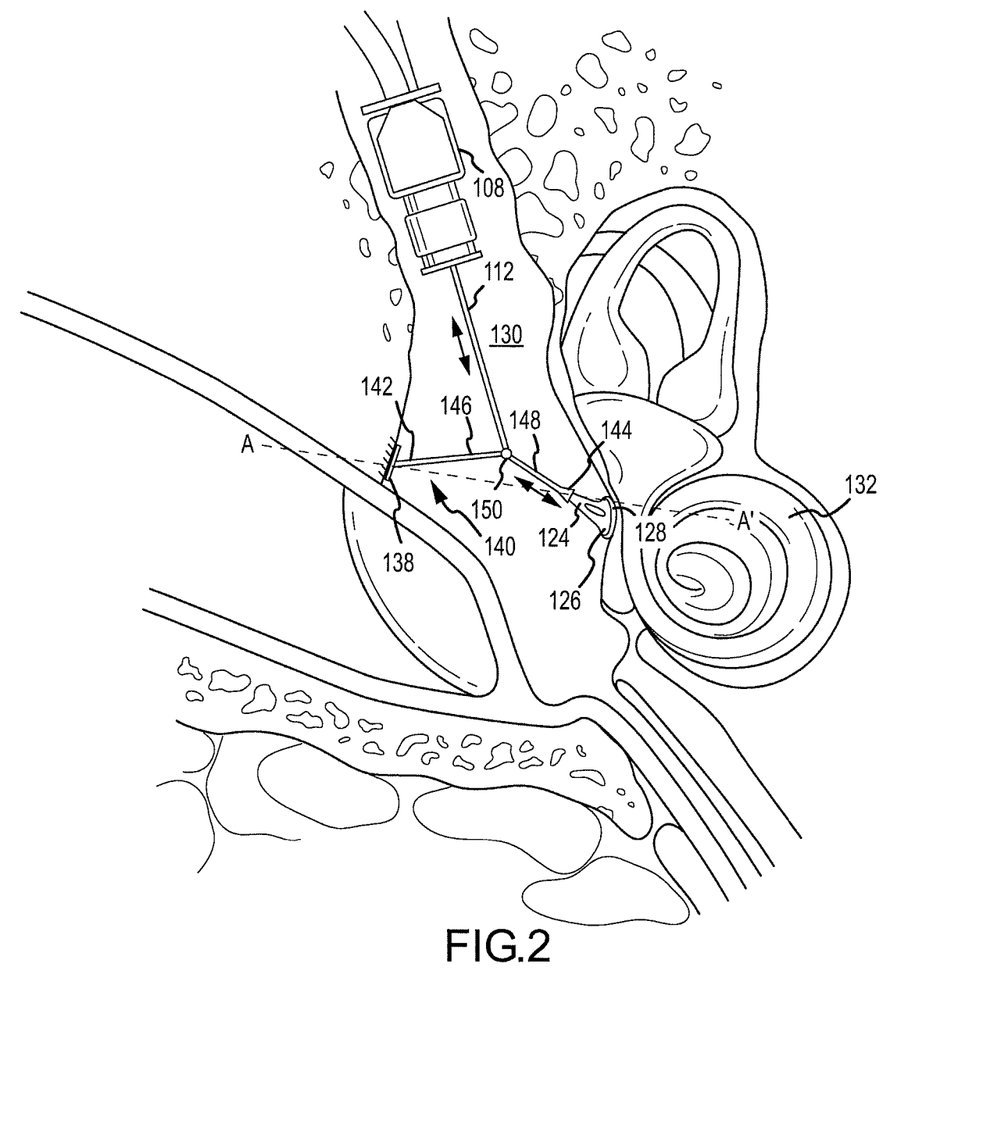
FIG. 2 illustrates a first embodiment of a spanning connector.

The footplate of stapes 124 rests against the oval window 128. Further, the stapes 124 function similar to a piston to displace fluid within the cochlea 132 behind the oval window. In this regard, up and down movement of the stapes 124 substantially normal to the interface of the stapes footplate and oval window typically provides the most effective transfer of energy to the oval window and cochlea. Such normal or 'natural movement' is typically present in a normal healthy ear. That is, vibrations of the tympanic membrane (e.g., caused by ambient sound) are transmitted to the stapes by the malleus and incus. One difficulty that arises in interconnecting a vibratory actuator 112 to the ossicular chain is that positioning the actuator 112 (e.g., through the mastoid process) is often driven by the location of the ear canal of the patient. In this regard, the long axis of the vibratory actuator 112, which often corresponds to the linear movement of the actuator, may not align with the direction of natural movement of an auditory component. Accordingly, the auditory component may be vibrated in an atypical manner, which may fail to generate efficient up and down motion of the stapes/oval window interface.

Accordingly, a connection apparatus is provided to interconnect the vibratory actuator 112 to an auditory component such that natural or near natural movement of the auditory component is produced via the axial movement of the actuator. That is, the connection apparatus translates the axial movement of the vibratory actuator 112 into a direction that is more natural for an auditory component. To achieve such translation, a spanning connector 140 is utilized. See FIG. 2.

The spanning connector 140 is adapted to extend across a portion of the tympanic cavity 130 such that a first end 142 of the spanning connector 140 may be affixed or otherwise anchored relative to a stationary middle ear structure and a second end 144 may engage an auditory component. The spanning connector 140 is typically positioned such that the vibratory actuator 112 engages a body portion of the spanning connector 140 between its first and second ends. The vibratory actuator 112 may move axially against the spanning connector 140. Accordingly, the spanning connector 140 may deflect in a direction aligned with the vibratory axis of the actuator 112. As the first end 142 of the spanning connector 140 is fixedly connected to a middle ear structure, the second end 144 may deflect in response to the axial vibrations and thereby stimulate the auditory component with which it is engaged.

The spanning connector 140 may be shaped and/or positioned such that the second end 144 displaces the auditory component in a natural or nearly natural direction. That is, in the case of the stapes 124, the stapes may be moved in a direction that is substantially normal to the interface between the stapes footplate 126 and the oval window 128. Of note, in the embodiment shown in FIG. 2, the incus and malleus are absent from the patient. These ossicle bones may be absent due to disease, or, these bones may have been removed surgically. While primarily being utilized in instances when a portion of the ossicle chain is removed, it will be appreciated that the spanning connector 140 may also be utilized in instances where all or a portion of the ossicular chain remains. In this regard, the second end of the spanning connector 140 may rest against any auditory component including, without limitation, the incus, the malleus and/or the stapes as well as the oval window and/or round window. The second end 144 of the spanning connector may interconnect and/or rest against the auditory component in any appropriate manner.

Figure 3A:
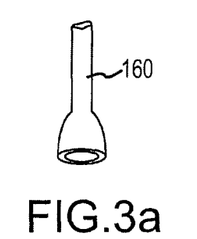
FIGS. 3A-F illustrates multiple embodiments of contacting ends for a spanning connector.
Figure 3B:
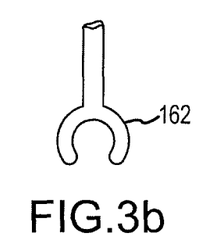
Figure 3C:
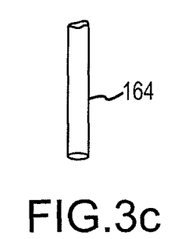
Figure 3D:
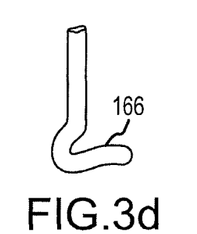
Figure 3E:
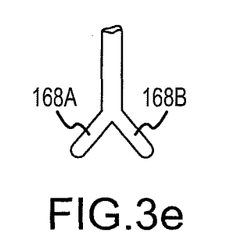
Figure 3F:
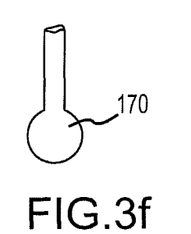

Various alternatives exist for contacting the second end 144 of the spanning connector 140 to an auditory component. As shown in FIG. 3A, the second end 144 of the spanning connector 140 is formed as a cup 160 that is sized to receive the head of the stapes. Surface adhesion due to the moist environment of the tympanic chamber may provide a connecting force between the cup 160 and stapes, or, an adhesive may be utilized to affix these members. In another arrangement illustrated in FIG. 3B, the second end 142 of connector member 134B is formed as a spring clamp. The clamp is formed as a C-shaped member 162 that has an internal size slightly smaller that the diameter of an auditory ossicle bone over which it may be disposed. Accordingly, when the ossicle bone is inserted into the clamp, a clamping force is created between the C-shaped member 162 and the ossicle bone. In the embodiment of FIG. 3C the second end 144 of the spanning connector 140 is formed as a straight wire 164. This straight wire may be utilized to engage the stapes footplate when the remainder of the stapes is missing. According to this embodiment, a shallow aperture may be formed in the footplate using an appropriate instrument, such as a laser or drill. In this regard, a mechanical coupling may be achieved through the healing process following insertion of the straight wire connector in the hole, e.g., by bone growth or tissue growth therebetween. In the embodiment of FIG. 3D, the second end 144 of the spanning connector is formed of a curved surface 166 that may rest against the surface of an auditory component. In the embodiment of FIG. 3E, the second end 144 of the spanning connector includes a notched connector that may receive a portion of an auditory component between first and second legs 168A, 168B. In the embodiment of FIG. 3F, the second end of the connector is formed as a ball 170. Such a second end may be beneficial when the spanning connector 140 is utilized to directly engage the oval or round windows. Other embodiments for contacting the second end of the spanning connector with an auditory component are possible and considered within the scope of the present invention.

The first end of the spanning connector 140 is typically fixedly connected to a stationary portion of the middle ear anatomy. See FIG. 2. For instance, the first end 142 may be adhered or affixed (e.g., screwed or sutured) relative to an inside surface of, for example, the tympanic cavity. It will also be appreciated that the first end 142 of the connector 140 may further include a plate 138 (which may be integral with the second end) that may be affixed to a middle ear structure (e.g., bony wall). The first end of the connector may include one or more apertures. Such apertures may allow a fastener to connect the connector to the bony wall and/or permit oseointegration.

By affixing a first end 142 of the connector 140 to the structure of the middle ear the second end 144 of the connector 140 may be moved relative to the auditory component by displacing a center portion of the connector 140. That is, the vibratory actuator 112 may be positioned against and/or connected to a mid-portion of the spanning connector 140 in order to apply axially vibrations thereto. In order to translate the axial vibrators of the actuator from a first direction to a second direction that is at least partially transverse to the first director, the spanning connector is generally nonlinear between its first and second ends 142, 144. That is, a portion of the body of the connector 140 is offset from a reference line A-A' that extends between the first and second ends 142, 144.

By applying an axial vibration to the central portion of the nonlinear connector, the second end 144 that interfaces with the auditory component may be moved (i.e., flexed) in a direction that is partially transverse to the direction of actuator movement. As will be appreciated, this may translate the axial movement of the actuator 112 into a direction that may be more aligned with the natural direction of movement of the auditory component. For instance, as shown the auditory component is the stapes footplate 126 and the spanning connector 140 allows for movement of the footplate 126 in a direction that is substantially normal with the interface between the footplate 126 and the oval window 128 similar to movement that is present in a normal healthy ear.

As shown in the embodiment of FIG. 2, a spanning connector 140 further includes a joint 150. This joint 150 may be a mechanical joint (e.g., hinge) or a flexible joint (e.g., elastomeric member, living hinge, etc.) that interconnects first and second separate portions 146, 148 of the spanning connector 140. Use of such a joint 150 may allow for aligning the second end 144 of the connector 140 with an auditory component. Further, such a joint may allow the second end of the connector to better translate the axial movement of the actuator into a desired direction such as, for example, along the axis of the second portion 148 of the connector. Additional joints may be utilized as well. For instance, a joint may connect elements to provide additional flexibility.

Figure 4:
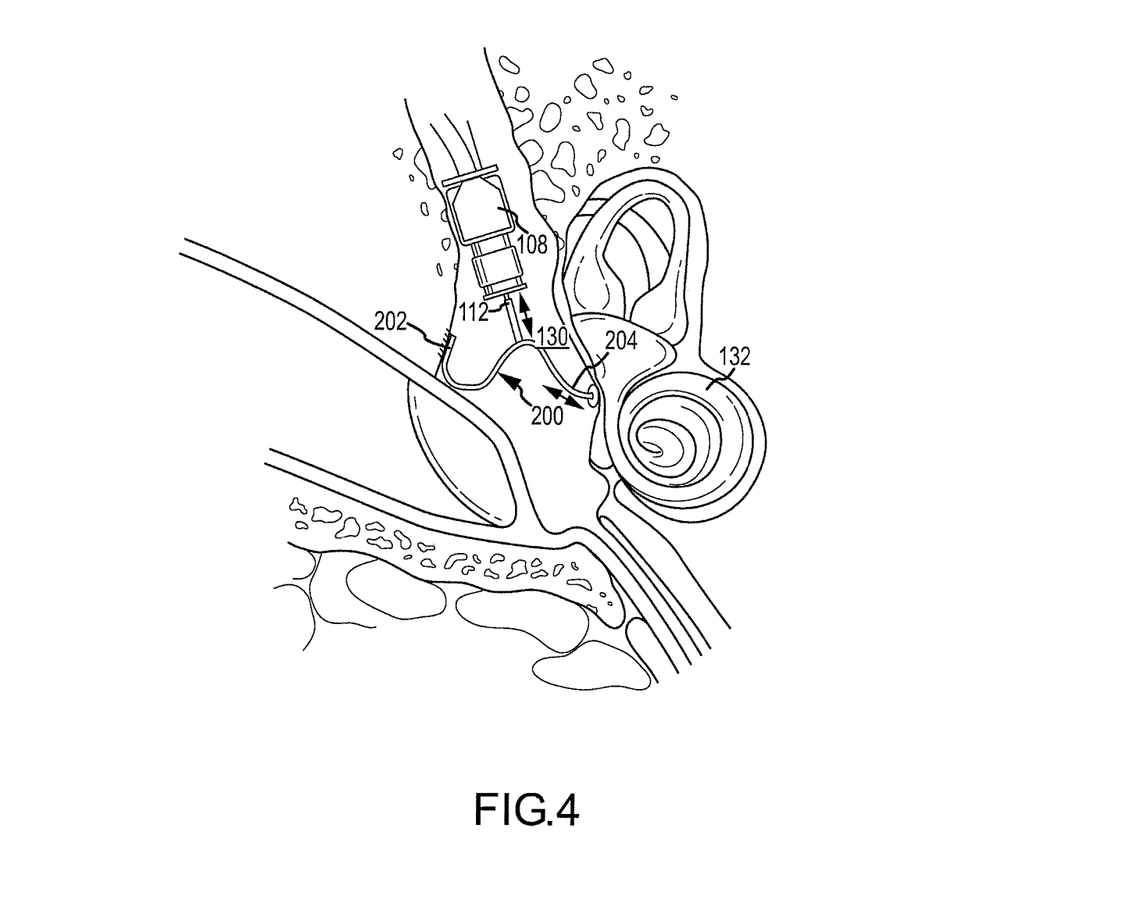
FIG. 4 illustrates a second embodiment of a spanning connector.

FIG. 4 illustrates a further embodiment of a spanning connector 200. In this embodiment, the connector 200 is a continuous flexible structure. Again, the first end 202 may be affixed to the interior of the middle ear structure, and the second end 204 may be placed against an auditory component of interest. In such an arrangement, the connector may be preformed or formed to a desired shape during installation to allow engagement with the tympanic cavity wall, the auditory component and/or the tip of the vibratory actuator 112. Again, by pressing on the center portion of the connector 200, the actuator may move an auditory component in a more natural direction.

To permit the connector 200 to be formed to a desired shape and then translate the movement of the actuator 112, it may be desirable that the connector be plastically deformable to a desired shape and then be elastically deformable in response to the movement of the vibratory actuator. The term "elastically deformable" refers to the deformation of a body caused by an applied stress, where the body returns to its original shape after the stress is removed. In this regard, the connector may act similar to a spring. In contrast, the term "plastically deformable" refers to the deformation of a body caused by an applied stress, where the deformation remains after the stress is removed. In the present embodiment, the spanning connector may be both plastically deformable (i.e., to define a desired shape for a particular application) and elastically deformable to transmit vibrations in use. That is, a surgeon may plastically deform the connector 200 to a desired shape. However, once bent to the desired or static shape, the connector 200 may be elastically deformed in response to the actuator movements. In this regard, by removing a deflection applied by the actuator, the connector may move back to its static shape.

Figure 5:
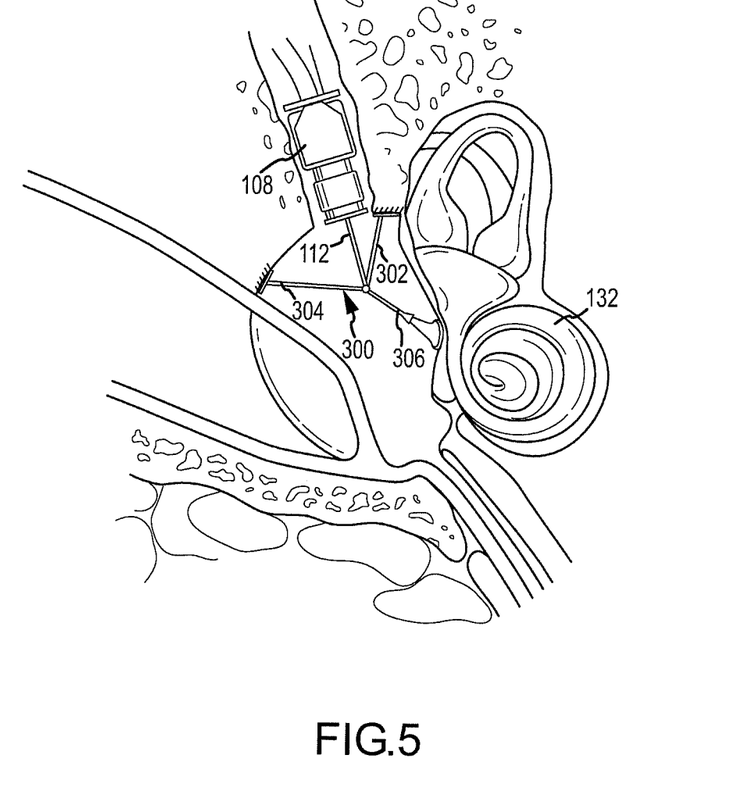
FIG. 5 illustrates a third embodiment of a spanning connector.

FIG. 5 illustrates a further embodiment of a spanning connector 300 having two support legs 302 and 304 and an actuating leg 306. In this embodiment, the actuator 112 may interconnect to the connector 300 near the point of connection of the two support legs 302, 304 and the actuating leg 306. In this regard, the first and second legs 302, 304 may be attached to the internal ear structure in a manner that directs movement of the actuating leg in a predetermined direction. That is, use of first and second support legs may allow for more controlled deflection of the second end of the actuating leg when the connector 300 is moved by the vibratory actuator 112.

Figure 6:
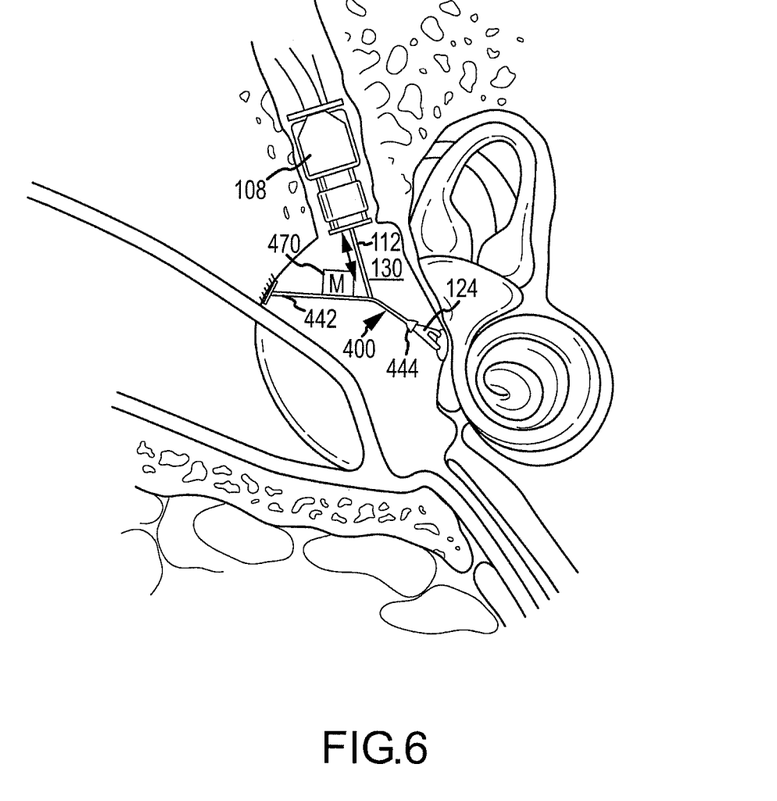
FIG. 6 illustrates a fourth embodiment of a spanning connector.

FIG. 6 illustrates a further embodiment of the present invention. As illustrated, the spanning connector 400 is a cantilevered member having a first end 442 interconnected to a bony wall of the middle ear structure and a second end 444 that engages an auditory component 124. In this embodiment, the spanning connector is a rigid body. Accordingly, by pressing the rigid body along its length, the connector may deflect and move the cantilevered second end 444 and hence the auditory component. In such an arrangement, a mass 470 may be added to the cantilevered spanning connector 400. In this regard, the spanning connector may be mass loaded to provide frequency shaping. For instance, by loading the cantilevered member, the sensitivity of the connector to various excitation frequencies may be increased or reduced. In this regard, the connector member may be utilized to enhance or reduce the conductance of certain frequencies to the auditory component.

In any of the above-noted arrangements, it may be desirable that the interconnection between the actuator 112 and the body portion of the connector be maintained. Any interconnection between these elements may be utilized. In one arrangement, the center portion of the connector may include a plurality of recesses and/or apertures that are sized to receive the engagement tip of the actuator 112. Such recesses or apertures may be spaced along the length of a central portion of the connector. In other arrangements, a clip may be utilized to fixedly interconnect these elements together. In embodiments where the actuator 112 is fixedly connected to the connector (i.e., utilizing a clip or other fastening connection), the actuator 112 may be operative to apply positive and negative displacement to the second end of the connector. That is, the actuator 112 may be operative to retract the connector as well as push on the connector. As will be appreciated, this may permit the application of increased amplitude displacements of the stapes/oval window interface and thereby provide additional auditory stimulation.

Those skilled in the art will appreciate variations of the above-described embodiments that fall within the scope of the invention. For instance, it may be advantageous to provide a transducer that produces vibratory movement in a direction that is not aligned/parallel to the long axis of the transducer. As a result, the invention is not limited to the specific examples and illustrations discussed above.

The invention claimed is:

1. A hearing prosthesis, including:
   a hearing implant actuator; and
   a connector for transmitting movement of the hearing implant actuator to an auditory component of a patient, the connector comprising:
   an elongate body having:
      a first end adapted for fixed attachment to a supporting structure; and
      a second end adapted to engage an auditory component,
   wherein said elongate body extends between said first and second ends and at least a portion of said elongate body is offset from a reference line extending between said first and second ends, and
   wherein the hearing implant actuator is connected to the connector between the first and second ends.

2. The hearing prosthesis of claim 1, further comprising:
   an actuator engagement surface disposed along said elongate body between said first and second ends for engaging the hearing implant actuator.

3. The hearing prosthesis of claim 2, wherein said actuator engagement surface comprises a recess formed into said elongate body.

4. The hearing prosthesis of claim 2, wherein said actuator engagement surface comprises at least one aperture formed into said elongate body.

5. The hearing prosthesis of claim 1, wherein at least a portion of said elongate body between said first and second ends is arcuate, defining an arcuate portion of said elongate body.

6. The hearing prosthesis claim 5, further comprising:
   an actuator engagement surface disposed along said arcuate portion.

7. The hearing prosthesis of claim 1, wherein said elongate body is elastically deformable in response to a force to be applied to said at least one portion of said elongate body.

8. The hearing prosthesis of claim 1, wherein application of a force to said at least a portion of said body in a first direction displaces said second end in a second direction that is at least partially transverse to the first direction.

9. The hearing prosthesis of claim 1, wherein said elongate body further comprises:
   a first linkage including said first end;
   a second linkage including said second end; and
   a joint interconnecting adjacent ends of said first and second linkages, wherein said joint permits relative movement between said first and second linkages.

10. The hearing prosthesis of claim 9, wherein said joint comprises a hinge.

11. The hearing prosthesis of claim 10, wherein said hinge comprises a living hinge.

12. The hearing prosthesis of claim 9, wherein:
   the implant actuator is a mechanical actuator,
   the implant actuator includes an output shaft that is a separate component from the components that make up the elongate body,
   the output shaft is linked to one of the joint, the first linkage member or the second linkage member, and
   the connector is configured to translate movement of the output shaft to an auditory component.

13. The connector of claim 1, wherein irrespective of the presence or absence of any transducer, the first end is attached to structure of the middle ear of a recipient of the connector at a location just above the tympanic membrane, and wherein the second end is attached to the auditory component.

14. The hearing prosthesis of claim 1, wherein the elongate body includes a joint located between the first end and the second end.

15. The hearing prosthesis of claim 1, wherein the connector is configured such that when an active ear implant applies a first stimulus to the elongate body in a first direction displacing the center portion of the elongate body, a second stimulus is applied to the second end of the elongate body in a second direction different from the first direction.

16. The hearing prosthesis of claim 1, wherein said elongate body comprises:
   a first linkage including said first end;
   a second linkage including said second end, wherein
   the first and second linkages are connected together at a joint, and
   the first and second linkages are configured such that respective lengths thereof are fixed.

17. The hearing prosthesis of claim 1, wherein:
   the implant actuator is a mechanical actuator,
   the implant actuator includes an output shaft that is a separate component from components that make up the elongate body, and
   the connector is configured to translate movement of the output shaft to an auditory component.

18. The hearing prosthesis of claim 17, wherein:
   the output shaft is linked to the elongate body at a first location so as to establish a three-way junction between the output shaft, a first portion of the elongate body on one side of the first location and a second portion of the elongate body on an opposite side of the first location from the first portion.

19. A connector for use in translating movement of an implant actuator to an auditory component, the connector comprising:
   a first linkage member with first and second ends, the first end of the first linkage member adapted to fixedly engage a first portion of a middle ear of a user;
   a second linkage member with first and second ends, the first end of the second linkage member adapted to be positioned relative to an auditory component of the middle ear of the user;
   a joint connecting the second ends of the first and second linkage members;

whereby when an active ear implant applies a first stimulus to one of the linkage members or the joint in a first direction, a second stimulus is applied to the first end of the second linkage member in a second direction that is at least partially transverse to the first direction.

20. The connector of claim 19, wherein the joint comprises a flexible region.

21. The connector of claim 20, wherein said flexible region is integrally formed with said first and second linkage members.

22. The connector of claim 19, wherein the connector further comprises:
a third linkage member with first and second ends, the first end of the third linkage member adapted to be mounted to a second portion of a middle ear of a user; and
wherein the joint is additionally mounted to the second end of the third linkage member.

23. The connector of claim 19, wherein the connector is configured such that when the active ear implant applies the first stimulus to one of the linkage members or the joint in the first direction displacing the center portion of the connector, the second stimulus is applied to the first end of the second connection linkage in the second direction.

24. The connector of claim 19, wherein the first end of the first linkage member is fixedly engaged with a structure of the middle ear of a recipient of the connector at a location just above the tympanic membrane, and wherein the first end of the second linkage member is fixedly engaged with the auditory component.

25. A hearing prosthesis comprising:
an actuator; and
the connector of claim 19, wherein the actuator is connected to the connector between the first end of the first linkage member and the first end of the second linkage member.

26. A device, comprising:
the connector of claim 19; and
the implant actuator, the implant actuator having an output shaft, wherein the actuator is configured to move the output shaft, wherein
the output shaft is linked to one of the joint, the first linkage member or the second linkage member, and
the connector is configured to translate movement of the output shaft to an auditory component.

27. The connector of claim 19, wherein the connector is configured such that when a mechanical actuator applies a first stimulus to one of the linkage members or the joint in a first direction in response to a signal thereto based on speech captured by a microphone, a second stimulus is applied to the first end of the second linkage member in a second direction that is at least partially transverse to the first direction, the stimulus evoking a hearing percept corresponding to the speech captured by the microphone.

28. The connector of claim 19, wherein the connector is configured such that application of a first stimulus to one of the linkage members or the joint in a first direction in response to a signal thereto based on speech captured by a microphone results in a second stimulus applied to the first end of the second linkage member in a second direction that is at least partially transverse to the first direction, the stimulus evoking a hearing percept corresponding to the speech captured by the microphone.

29. An at least partially implantable hearing instrument for transmitting movement of a hearing implant actuator to an auditory component of a patient, comprising:
an elastic member having a first end adapted for interconnection to a stationary middle ear structure and a second end adapted for interconnection to an auditory component, wherein in a substantially non-biased state said elastic member applies a static load between said stationary middle ear structure and said auditory component; and
an actuator physically engaging said elastic member, said actuator being operative to move in at least a first direction to apply a biasing force to said elastic member, wherein said second end of said elastic member moves in a second direction in response to said biasing force, wherein said first and second directions are at least partially transverse.

30. The instrument of claim 29, wherein the instrument is configured such that when the actuator moves in at least the first direction displacing a center portion of the elastic member and applying a biasing force to the elastic member, said second end of said elastic member moves in the second direction in response to the biasing force.

31. The instrument of claim 29, wherein the first end is interconnected with structure of the middle ear of a recipient of the instrument at a location just above the tympanic membrane, and wherein the second end is interconnected to the auditory component.

32. The instrument of claim 29, wherein the actuator is attached to the elastic member between the first end and the second end.

33. The instrument of claim 29, wherein the elastic member is configured to span an entire distance across an inner ear cavity irrespective of the presence or absence of the actuator.

* * * * *